US011344520B2

(12) United States Patent
Frangione et al.

(10) Patent No.: US 11,344,520 B2
(45) Date of Patent: *May 31, 2022

(54) EFFECTS OF HEPARIN ON TOPICAL USE OF PLASTERS CONTAINING A NON-STEROIDAL ANTI-INFLAMMATORY DRUG

(71) Applicant: ALTERGON SA, Lugano (CH)

(72) Inventors: Valeria Frangione, Lugano (CH); Arturo Lanzarotti, Lugano (CH)

(73) Assignee: ALTERGON SA, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/322,151

(22) Filed: May 17, 2021

(65) Prior Publication Data

US 2021/0267925 A1 Sep. 2, 2021

Related U.S. Application Data

(63) Continuation of application No. 17/135,864, filed on Dec. 28, 2020, which is a continuation of application No. 14/627,036, filed on Feb. 20, 2015, now Pat. No. 10,905,669.

(51) Int. Cl.
| | |
|---|---|
| *A61K 31/196* | (2006.01) |
| *A61L 15/58* | (2006.01) |
| *A61K 31/727* | (2006.01) |
| *A61F 13/00* | (2006.01) |
| *A61L 15/28* | (2006.01) |

(52) U.S. Cl.
CPC ...... *A61K 31/196* (2013.01); *A61F 13/00063* (2013.01); *A61K 31/727* (2013.01); *A61L 15/28* (2013.01); *A61L 15/58* (2013.01); *A61L 2300/41* (2013.01); *A61L 2300/802* (2013.01)

(58) Field of Classification Search
CPC .. A61K 31/196; A61K 31/727; A61L 2300/41
See application file for complete search history.

(56) References Cited

U.S. PATENT DOCUMENTS

| | | | |
|---|---|---|---|
| 6,592,891 B1 | 7/2003 | Donati et al. | |
| 6,669,953 B1 | 12/2003 | Kamiyama | |
| 7,799,338 B2 * | 9/2010 | Donati | A61K 31/727 |
| | | | 424/448 |
| 2003/0203017 A1 | 10/2003 | Donati et al. | |
| 2005/0048101 A1 | 3/2005 | Donati et al. | |

OTHER PUBLICATIONS

Constantino, Clin Drug Investig, 31, 1,2011 (Year: 2011).*
Affaitati, et al., "A Randomized, Controlled Study Comparing a Lidocaine Patch, a Placebo Patch, and Anesthetic Injection for Treatment of Trigger Points in Patients with Myofascial Pain Syndrome: Evaluation of Pain and Somatic Pain Thresholds," Clinical Therapeutics vol. 31, No. 4 2009: 705-720.
Affaitati, et al., "Effects of Topical Diclofenac (DHEP Plaster) on Skin, Subcutis and Muscle Pain Thresholds in Subjects without Spontaneous Pain," Drugs Exptl. Clin. Res. XXVII(2) 69-76 (2001).
Banning M., "Topical Diclofenac: Clinical Effectiveness and Current Uses in Osteoarthritis of the Knee and Soft Tissue Injuries," Expert Opin. Pharmacother. (2008) 9(16):2921-2929.
Brewer et al., "Updated on the Use of Topical NSAIDs for the Treatment of Soft Tissue and Musculosketela Pain: A Review of Recent Data and Current Treatment Options", The Physician SportsMedicine, Jun. 2010, No. 2, vol. 38: 61-70.
Bruhlmann, et al., "Short-Term Treatment with Topical Diclofenac Epolamine Plaster in Patients with Symptomatic Osteoarthritis: Pooled Analysis of Two Randomised Clinical Studies," Current Medical Research and Opinions, vol. 22, No. 12, 2006, 2429-2438.
Costantino, et al., "Diclofenac Epolamine Plus Heparin Plaster versus Diclofenac Epolamine Plaster in Mild to Moderate Ankle Sprain," Clin Drug Investig 2011; 31(1): 15-26.
Coudreuse, et al., "Effect of a Plaster Containing DHEP and Heparin in Acute Ankle Sprains with Oedema: a Randomized, Double Blind, Placebo-Controlled, Clinical Study," Current Medical Research & Opinion, vol. 26, No. 9, 2010, 2221-2228.
Dragani, et al., "Effetti di un'Associazione Eparina-Eparinoide Sulle Modificazioni Estesiologiche e Trofiche dei Tessuti Periarticolari Profondi in Corso di Gonartrosi," European Review for Medical and Pharmacological Sciences 1992; XIV; 271-277.
Dragani, et al., "L'associazione Eparina-Glucoronilglucosaminoglicano per Uso Topico," Mi Med 1989 80:397-403.
Folzer, E. et al., "Comparison of skin permeability for three diclofenac topical formulations: an in vitro study," Pharmazie, vol. 69, Jan. 2014, pp. 27-31.
Galer, et al., "Topical Diclofenac Patch Relieves Minor Sports Injury Pain: Results of a Multicenter Controlled Clinical Trial," Journal of Pain and Symptom Management, vol. 19 No. 4, Apr. 2000 287-294.
Giamberardino, "Mise en Evidence de l'Activite' Pharmacodynamique de Flector Tissugel(r) 1% Chez Des Volontaires Sains et Des Patients Souffrant de Gonarthrose," Presse Med. 2004, 33:355-359.
Gimbel, et al., "Effectiveness and Safety of Diclofenac Epolamine Topical Patch 1.3% for the Treatment of Acute Pain Due to Back Strain: An Open-Label, Uncontrolled Study," The Physician and SportsMedicine, Feb. 2011, No. 1, vol. 39:1-8.
Haroutiunian, et al., "Topical NSAID Therapy for Musculoskeletal Pain," Pain Medicine 2010; 11: 535-549.
Hoffmann, et al., "Efficacy and Tolerability of DHEP-Heparin Plaster in Reducing Pain in Mild-To-Moderate Muscle Contusions: A Double-Blind, Randomized Trial," Current Medical Research & Opinion vol. 28, No. 8, 2012, 1313-1321.

(Continued)

*Primary Examiner* — Susan T Tran
*Assistant Examiner* — William Craigo
(74) *Attorney, Agent, or Firm* — Fenwick & West LLP

(57) ABSTRACT

The present invention provides for a method of improving the release of non-steroidal anti-inflammatory drugs (NSAIDs) from a plaster or bandage comprising an adhesive layer with a pharmaceutically acceptable NSAID together with heparin or a heparinoid. The invention also provides for methods of reducing muscle hyperalgesia in subjects without spontaneous pain.

8 Claims, 1 Drawing Sheet

(56) References Cited

OTHER PUBLICATIONS

Klainguti, et al., "A Plaster Containing DHEP and Heparin for Mild to Moderate Contusions and Sprains with Haematoma: A double-Blind Randomized Study," Current Medical Research & Opinion vol. 26, No. 9, 2010, 2243-2251.

Kneer, et al., "A Multiple-Dose, Open-Label, Safety, Compliance, and Usage Evaluation Study of Epicutaneously Applied Diractin(R) (Ketoprofen in Transfersome(R) in Joint/Musculoskeletal Pain or Soft Tissue Inflammation," Current Drug Safet, 2009, 4, 5-10.

Kuehl, et al., "Analgesic Efficacy and Safety of the Diclofenac Epolamine Topical Patch 1.3% (DETP) in Minor Soft Tissue Injury," Sports Med 2011; 32:635-643.

Laboratoires Genevrier, "Full Legal Notice Flector Tissugel Heparine. RTM.," seven pages (Jul. 21, 2014 is listed within the document as a potential document date; date of public availability not determined).

Lionberger, et al. "Diclofenac Epolamine Topical Patch Relieves Pain Associated with Ankle Sprain," Journal of Pain Research, 2011:4 47-53.

Lionberger, et al., "Topical Nonsteroidal Anti-Inflammatory Drugs for the Treatment of Pain Due to Soft Tissue Injury: Diclofenac Epolamine Topical Patch," Journal of Pain Research, 2010: 3 223-233.

Mahler, et al., "Double-Blind, Randomized, Controlled Study on the Efficacy and Safety of a Novel Diclofenac Epolamine Gel Formulated with Lecithin for the Treatment of Sprains, Strains and Contusions," Drugs Exptl. Clin. Res. XXIX(1) 45-52 (2003).

Mazieres, et al., "Topical Ketoprofen Patch in the Treatment of Tendinitis: A Randomized, Double Blind, Placebo Controlled Study," J. Rheumatol 2005; 32:1563-70.

McCzarberg, et al., "Topical Diclofenac Epolamine Patch 1.3% for the Treatment of Acute Pain Caused by Soft Tissue Injury," Int. J. Clin Pract May 2010: 1-8.

NG, S-F. et al., Validation of a Static Franz Diffusion Cell System for In Vitro Permeation Studies, AAPS PharmSciTech, vol. 11, No. 3, Sep. 2010, pp. 1432-1441.

Petersen et al., "Diclofenac Epolamine (Flector(R)) Patch, Evidence for Topical Activity", Clin Drug Invest 2009; 29(1): 1-9.

Rainsford, et al., "Review of the Pharmaceutical Properties and Clinical Effects of the Topical NSAID Formulation, Diclofenac Epolamine," Curr Med Res Opin 2008; 24(10): 2967-2992.

United States Office Action, U.S. Appl. No. 16/696,583, dated Feb. 24, 2020, 20 pages.

Woolf, "Central Sensitization: Implications for the Diagnosis and Treatment of Pain," Pain, Mar. 2012; 152 (3 Suppl): S2-15 1-31.

Yanchick et al., "Time to Significant Pain Reduction Following DETP Application vs Placebo for Acute Soft Tissue Injuries," vol. 26, No. 8, 2010, 1993-2002.

United States Office Action, U.S. Appl. No. 14/627,036, filed Feb. 20, 2020, 22 pages.

United States Office Action, U.S. Appl. No. 14/627,036, filed Nov. 15, 2018, 32 pages.

United States Office Action, U.S. Appl. No. 14/627,036, filed Apr. 3, 2018, 25 pages.

United States Office Action, U.S. Appl. No. 14/627,036, filed Sep. 1, 2017, 19 pages.

United States Office Action, U.S. Appl. No. 14/627,036, filed Jan. 12, 2017, 11 pages.

United States Office Action, U.S. Appl. No. 14/627,036, filed Aug. 2, 2016, 16 pages.

* cited by examiner

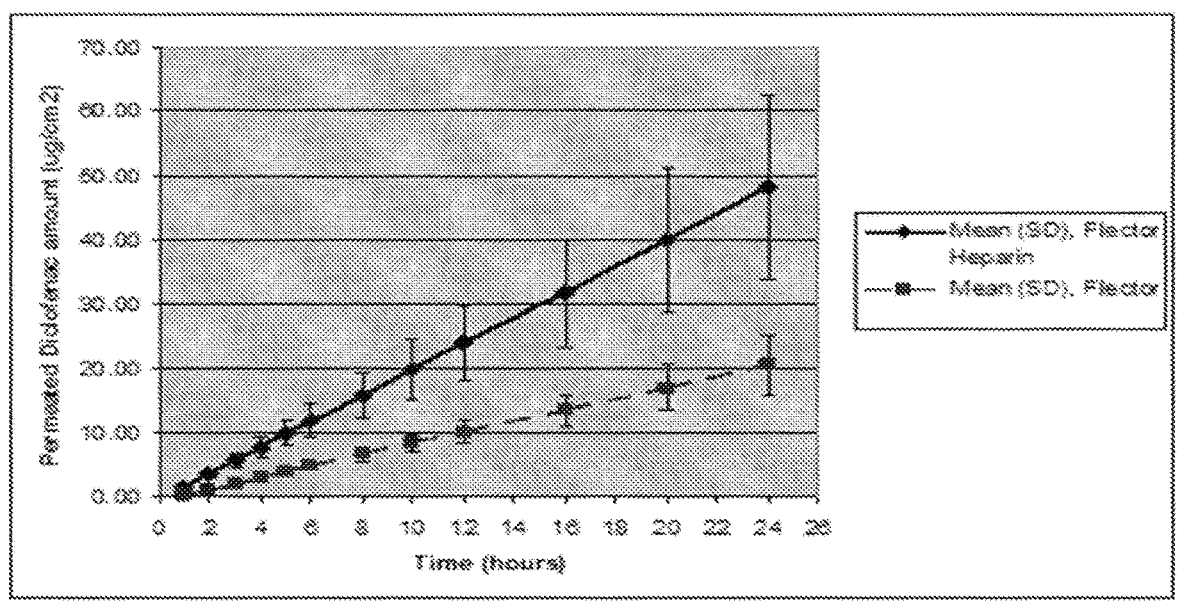
Mean (± SD) permeation profiles of diclofenac (expressed as DHEP) from Flector® Patch and Flector-Heparin Patch.

EFFECTS OF HEPARIN ON TOPICAL USE OF PLASTERS CONTAINING A NON-STEROIDAL ANTI-INFLAMMATORY DRUG

CROSS REFERENCE TO RELATED APPLICATIONS

This application is a continuation of and claims the benefit of U.S. patent application Ser. No. 17/135,864, filed Dec. 28, 2020, which is a continuation of and claims the benefit of U.S. patent application Ser. No. 14/627,036, filed Feb. 20, 2015, all of which are hereby incorporated in its entirety by reference.

FIELD OF INVENTION

Plasters for topical use having an analgesic activity and being able to induce the reabsorption of hematomas, containing a non-steroidal anti-inflammatory drug in association with heparin or a heparinoid.

PRIOR ART

U.S. Pat. Nos. 6,592,891 and 7,799,338, incorporated herein by reference in their entireties, describe plasters for topical use having an analgesic activity and at the same time being capable to induce reabsorption of hematomas.

These plasters comprise a substrate layer, an adhesive layer in the form of a hydrogel matrix containing a pharmaceutically acceptable non-steroidal anti-inflammatory drug ("NSAID"), heparin or a heparinoid and a protective film which can be removed at the moment of use.

Applicants have now surprisingly found that plasters containing NSAIDs mixed with heparin or a heparinoid are more effective in increasing pain thresholds to electrical stimulation of cutis, sub cutis and muscle in asymptomatic subjects with a latent algogenic condition compared to plasters containing NSAIDs only.

Moreover, Applicants have also surprisingly found that heparin or a heparinoid, without being released by the plaster in significant amount, is capable of increasing the release of the NSAIDs from the plaster and its permeation through a synthetic membrane.

DESCRIPTION OF THE INVENTION

It has been found that plasters comprising heparin and a NSAID have a better effect on pain thresholds to electrical stimulation of cutis, sub cutis and muscle when topically applied in subjects without spontaneous pain compared to plasters comprising NSAID only.

Moreover, it has also been found that heparin increases the permeability and the release of NSAID present on an adhesive layer of a plaster without being released by the plasters.

BRIEF DESCRIPTION OF THE DRAWINGS

FIG. 1 shows the permeation profiles of diclofenac from Flector® Patch and Flector-Heparin Patch.

DETAILED DESCRIPTION OF THE INVENTION

It has surprisingly been found that the use of heparin or a heparinoid on a plaster or bandage together with a NSAID improves the release of the NSAID from the plaster.

It has also surprisingly been found that the presence of heparin or a heparinoid on a plaster or bandage increases the membrane permeability of the NSAID.

Moreover, unexpectedly, Applicants have also found that topical applications of a plaster or bandage containing heparin, or heparinoid together with a NSAID are more effective in reducing muscle hyperalgesia in subjects without spontaneous pain (as evidenced and quantified by the increase in pain threshold to external standardized electrical or pressure stimuli) than topical applications of plasters containing only a NSAID.

Accordingly, the present invention provides for methods of improving release of non-steroidal anti-inflammatory drugs (NSAIDs) from a bandage comprising:
  a) a substrate layer;
  b) an adhesive layer in the form of a polymeric hydrogel matrix comprising an effective amount of a pharmaceutically acceptable NSAID and heparin or a heparinoid, at least one thickening agent, at least one wetting agent, at least one cross-linking agent; and
  c) a protective film which can be removed at the moment of use, wherein said hydrogel matrix further comprises a surfactant consisting of sodium ethylenediamine tetraacetate; said method comprising
  topically applying said bandage to patients in need thereof, and
  assessing an improved NSAID release compared NSAID release from bandages without heparin.

The present invention provides also for methods of increasing membrane permeation of non-steroidal anti-inflammatory drugs (NSAID) from a bandage comprising:
  a) a substrate layer;
  b) an adhesive layer in the form of a polymeric hydrogel matrix comprising an effective amount of a pharmaceutically acceptable NSAID and heparin or a heparinoid, at least one thickening agent, at least one wetting agent, at least one cross-linking agent; and
  c) a protective film which can be removed at the moment of use, wherein said hydrogel matrix further comprises a surfactant consisting of sodium ethylenediamine tetraacetate; said method comprising:
    applying said bandage to a membrane; and
    assessing an increased membrane permeation of NSAID compared to membrane permeation obtainable from bandages without heparin.

It provides also for methods of reducing muscle hyperalgesia in subjects without spontaneous pain, said method comprising:
  assessing an initial pain threshold in said subjects;
  applying to said subjects a bandage comprising:
  a) a substrate layer;
  b) an adhesive layer in the form of a polymeric hydrogel matrix comprising a pharmaceutically acceptable NSAID and heparin or a heparinoid, at least one thickening agent, at least one wetting agent, at least one cross-linking agent; and
  c) a protective film which can be removed at the moment of use, wherein said hydrogel matrix further comprises a surfactant consisting of sodium ethylenediamine tetraacetate;
  reassessing the pain threshold; and
  determining a reduced muscle hyperalgesia in said subjects measured as a difference between the initial and the reassessed pain threshold.

According to one embodiment of the present invention, the NSAID is selected from the group consisting of diclofenac, diflunisal, ibuprofen, ketoprofen, naproxen, acetysalicic acid, salsalate, celecoxib, etodolac, fenoprofen, flurbiprofen, indomethacin, ketorolac, meloxicam, mefenamic acid, nabumetone, oxaprozin, piroxicam, rofecoxib, sulindac, tolmetin, valdecoxib or pharmaceutically acceptable salts thereof.

According to a particularly preferred embodiment the NSAID is diclofenac in the form of a pharmaceutically acceptable salt, and more preferably, it is a salt with a heterocyclic amine of general formula

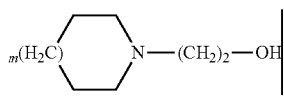

where m is 0 or 1.

According to a better embodiment, the heterocyclic amine is N-hydroxyethyl pyrrolidine (epolamine).

The diclofenac salt is contained in the plaster according to the present invention in concentrations generally ranging from 0.1 to 5 wt %, preferably in concentrations of between 0.3 and 3 wt % with respect to the total weight of the composition used for the preparation of the hydrogel matrix.

According to a particularly preferred embodiment, the concentration of the diclofenac salt is 1.3 wt % with respect to the total weight of the composition used for the preparation of the hydrogel matrix.

When the plaster according to the present invention contains a heparinoid, the latter preferably presents a molecular weight of between 5,000 and 30,000 DA.

The heparin or heparinoid is present in concentrations such that its total quantity in the plaster is between 0.05 and 1%, which corresponds respectively to a concentration range of between 1,400 and 28,000 IV/plaster (100-2,000 IU/g matrix). According to a particularly preferred embodiment, heparin is contained in concentrations such that the corresponding content is 5600 IU per plaster.

It is advisable that the composition used for preparing the hydrogel matrix should present pH values of between 7.2 and 9, preferably of between 7.5 and 8.5. At pH values lower than 7.2, the diclofenac crystals that are insoluble in water precipitate; values higher than 9 may cause irritation of the skin. To adjust the pH of the hydrogel composition, any organic or inorganic acid, or any organic or inorganic base may be used, without any particular limitation. The concentration of the above-mentioned acid or base is not critical either and may vary according to the pH value that the hydrogel composition reaches.

In addition to the aforementioned active principles, the hydrogel matrix further contains thickening agents, wetting agents, fillers, preservatives, cross-linking agents, surfactants, stabilizers, and the like.

Preferably, the composition used for the preparation of the hydrogel matrix contains as thickening agents the following: polyacrylic acid, sodium polyacrylate, sodium carboxymethyl cellulose, polyvinyl alcohol, polyvinyl pyrrolidone, gelatine or corresponding mixtures. The concentration of the above additives is generally between 3 and 30 wt %, preferably between 5 and 20 wt %. If the concentration is lower than 3 wt %, the viscosity of the composition is too low, so that the composition comes out of the plaster and remains on the skin once the plaster is applied; on the other hand, if the concentration is too high, it is not very workable. According to a particularly preferred embodiment, the thickening agents are a mixture consisting of the following: gelatine, polyvinyl pyrrolidone, sodium polyacrylate, and sodium carboxymethyl cellulose in a total concentration of 9 wt % with respect to the total weight of the hydrogel matrix. The hydrogel matrix of the plaster according to the present invention preferably comprises at least one wetting agent chosen from among glycerol, propylene glycol, polyethylene glycol, 1,3-butanediol, and an aqueous solution of D-sorbitol, preferably in a concentration of 70 wt %.

The concentration of the said wetting agents in the composition used for the preparation of the hydrogel matrix according to the present invention is between 5 and 70 wt %, preferably between 10 and 60 wt % with respect to the total weight of the composition used for the preparation of the hydrogel matrix.

If the quantity of wetting agent is lower than 5%, the wetting effect is not sufficient and the composition dries quickly; if, instead, the quantity of wetting agent is higher than 70%, mixing of the components is difficult.

The cross-linking agent is preferably an aluminum or calcium compound present in the composition used for the preparation of the hydrogel matrix in a concentration of between 0.01 and 3.0 wt %. If the quantity of this additive is lower than 0.01 wt %, cross-linking is insufficient, so that the resistance to heat of the hydrogel matrix is reduced; consequently, two drawbacks may occur, either during storage or during application: during storage, the composition is too fluid and comes out of the plaster in the sterile container in the sterile container of the latter; when the plaster is applied, the composition leaves a residue on the skin. When the concentration of the cross-linking agent is higher than 3%, the rate of cross-linking is too high and consequently the viscosity of the composition used for the preparation of hydrogel matrix increases, so that the corresponding workability decreases. As a filler, one of the following, for instance, may be used: kaolin, titanium dioxide, bentonite, or mixtures of the said compounds.

As a preservative, the hydrogel matrix that is the subject of the present invention may contain either preservatives of a conventional type, such as the esters of para-alkyloxy benzoic acid, for example Nipagin and Nipasol, or sorbic acid. The hydrogel matrix may possibly contain a surfactant, such as a polyoxyethylene sorbitan ester (Tween 80) and a stabilizer, such as sodium ethylenediamine tetraacetate. As far as the substrate layer is concerned, any material usually employed for this purpose may be used, such as fabric, non-woven fabric, paper, plastic film and corresponding laminates.

As regards the removable protective film, this may be of a conventional type, for instance, siliconized paper, or may be made of a plastic material, such as polyethylene, polyethylene terephthalate, or polyvinyl chloride.

The present plaster is prepared according to conventional methods which, in particular, envisage the following fundamental stages: mixing of the various components of the composition used for the preparation of the hydrogel matrix, co-extrusion of the hydrogel matrix between the substrate layer and the removable protective film.

The mixing phase is in particular conducted in the following stages: 1-A) mixing of one part of water with the filler and with part both of the cross-linking agent and of the thickening agent; 1-B) subsequent addition to the mixture obtained in stage (1-A) of further thickening agents; 1-C) addition to the mixture obtained in stage (1-B) of preservatives, a stabilizer, a pH adjuster, as well as of the remaining part of the cross-linking agent and thickening and wetting agents; 1-D) addition to the mixture obtained in stage (1-C)

of the pharmaceutically acceptable diclofenac salt; 1-E) addition to the mixture obtained in stage (1-D) of the heparin or heparinoid.

The preparation of the hydrogel matrix used as adhesive layer of the plaster according to the present invention is described in U.S. Pat. No. 6,592,891 and in U.S. Pat. No. 7,799,338 incorporated herein by reference in their entireties.

The following examples exemplify the methods described herein. The examples are for purposes of illustration only and are not intended to be limiting of the invention.

Example 1

Effect of Heparin on the In Vitro Permeability of Diclofenac Epolamine

Permeation of diclofenac epolamine (DHEP) was assessed in vitro with Flector® and Flector-Heparin patches by using a Franz Cell System.

According to the non parametric method of the FDA Guidance, the Flector-Heparin Patch is not equivalent to Flector® Patch in terms of DHEP release and permeability. Mean DHEP permeation flow rate over the 24 hours was higher from Flector-Heparin Patch than from Flector® Patch (2.01±0.60 vs. 0.86±0.19 µg/cm2/h).

Also, the cumulative amount of DHEP that crossed the Franz Cell silicone membrane over 24 hours was significantly greater from Flector-Heparin Patch than from Flector® Patch (48.23±14.37 vs. 20.54±4.68 µg/cm$^2$). Heparin did not appear to be released from the plaster.

In conclusion, the results of the in vitro permeation tests showed that heparin contained in Flector-Heparin Patch enhances DHEP permeation and suggest that an improved local anti-inflammatory and analgesic activity may be expected upon Fleeter-Heparin Patch application to the skin.

Applicants have developed two medicated patches containing diclofenac epolamine (DHEP) as an active ingredient, namely Flector Patch and Flector-Heparin Patch.

The two patches have identical qualitative and quantitative composition, except for the content of heparin sodium (40,000 IU/100 g of paste or 5,600 IV/plaster), a natural glycosaminoglycan obtained by extraction of porcine intestinal mucosa, which is present only in the Flector-Heparin Patch. Both patches consist of 14 g of paste, containing 181 mg of DHEP, applied to an unwoven cloth of 10 cm×14 cm in size (surface area 140 cm2).

According to the FDA guidance for Industry on Non sterile Semisolid Dosage Forms—CDER, May 1997(1), the evaluation of in vitro release of DHEP from topical dosage forms can be performed through the use of an open chamber diffusion cell system, i.e., a Franz Cell System, fitted with a synthetic membrane. This system was used to compare DHEP release and permeability from the two patches in an attempt to explain the role of heparin in the enhancement of clinical activity observed in several clinical trials performed to date. The release and permeability of heparin was also investigated.

The comparison of DHEP release from the two patches and membrane permeability was expected to demonstrate whether heparin, which is unlikely to be either released from the patch or permeate the skin barrier due to its high polarity, negative charge and molecular weight, may act as an enhancer of DHEP release from the patch, thus providing the medicated plaster with higher anti-inflammatory and analgesic activity when locally applied.

The study was conducted using a Franz Cell Apparatus equipped with a synthetic membrane. Concentrations of DHEP and heparin were determined by a validated HPLC method and a biological assay, respectively.

Equipment:

Permeation equipment: Franz Cell System. Standard, open cap, flat ground glass surface with 15 mm diameter orifice, total diameter of cell 25 mm, area 1.767 cm2 Microette Plus—Hanson; Multifill Hanson—Fraction Collector System Silicone membranes: Perouse Plastie, PlastiePerthese LP 800-5, 0.5 mm thickness, of appropriate size (25 mm diameter) to fit the diffusion cell. Lipophilic nonporous silicone membranes may be useful surrogate membranes for human skin when evaluating in vitro release characteristics of a drug from topical or transdermal patch formulations.

HPLC: Agilent 1200; software EXChrom Elite.
pH meter: Metrohm 827 pH lab.
Analytical Balance: Mettler XP105DR.
Spectrophotometer UV-Vis: Jasco V-630.
Vortex: IKA MS3.
Thermostatic Bath: Julabo basic.

For the assessment of DHEP permeability, the Reference patch (R, Flector®) and the Test patch (T, Flector-Heparin) were taken from their original envelopes (primary packaging) immediately before the study, cut into pieces with shape (circular) and size (25 mm diameter) corresponding to those of the synthetic membrane in order to properly fit them into the Franz cells.

The amount of DHEP in the Flector® Patch and the Flector-Heparin Patch is 181 mg, the total patch area is 140 cm2, and the amount of DHEP per surface unit is 1.293 mg/cm2 (corresponding to 1 mg/cm2 diclofenac sodium salt). Considering that the surface area of a donor Franz Cell orifice is 1.767 cm2 (cell permeation area), the amount of DHEP exposed to the silicone membrane per cell was 2.284 mg.

Samples of R and T were placed on the upper side of the membrane in the open donor chamber of the diffusion cell and a receptor medium (PBS pH 7.4, total volume 7 mL) was placed on the other side of the membrane in the receptor cell. Diffusion of DHEP from the patch samples across the membrane was monitored by assay of sequentially collected samples of receptor fluid. The removed aliquots of the receptor phase were replaced with fresh aliquots of the buffer. Each collected aliquot (total volume 2.5 ml, sample volume 1.0 mL) was immediately analyzed for DHEP content by HPLC. The amount of DHEP released from each sample of Flector w/wo Heparin was calculated by the following equation, which takes into account the amount of DHEP subtracted from the receiving buffer with sample withdrawals.

$$Q_n = \frac{\left[(C_n * 7) + \sum_{x=1}^{x=n-1} (C_x * V_p)\right]}{1.767}$$

Where:
$Q_n$=amount of drug permeated at time n (µg/cm 2);
$C_n$=DHEP concentration in sample taken at time n (µg/mL);
n=sampling times, i.e., 1, 2, 3, 4, 5, 6, 8, 10, 12, 16, 20, 24 hours;
7=total cell volume (mL);
$C_x$=DHEP concentration at time x (µg/mL), where x corresponds, at sampling time n, to sampling time n−1;

Vp=withdrawal volume (2.5 mL)=rinsing volume (1.5 mL)+sampling volume (1.0 mL);

1.767 (cm2)=cell permeation area (15 mm diameter).

In order to validate the synthetic membrane for the permeation of heparin, a preliminary experiment was conducted by placing a heparin solution in the 5 donor chambers (T) and determining the passage through the silicone membrane into the receiving chamber. Heparin solution in the donor chamber was constituted by 1 mL of a 70 IU/mL sodium heparin solution in PBS pH 7.4. The heparin solution concentration was consistent with the amount of heparin exposed to the silicone membrane when patch samples were tested. A blank sample (B, 1 mL of PBS pH 7.4, without heparin) was also placed in a donor chamber.

Heparin concentration was determined by a method recommended by USP 30, Official monographs, page 2274 (Heparin sodium—Anti-factor Xa, activity), using a Stachrom Heparin Kit (Diagnostica SIBSA TAGO). The method was adapted for application to Franz Cell permeated samples and validated. Briefly, heparin, in the presence of AT III (Antitrombin III) excess binds ATIII to form a complex. By adding the coagulation factor Xa, a three element complex is formed, together with the release of residual factor Xa. This residual factor hydrolyzes a chromogenic substrate, thus releasing para-nitroaniline (pNa) which is quantified by spectrophotometric analysis at $\lambda=405$ nm. The absorbance measured is inversely proportional to the heparin content in the sample. Maximum absorption is detected in the sample without heparin.

Heparin quantification was performed by constructing a 5-point linear calibration curve with a concentration range of 0.10-0.50 IU/mL. At the beginning of analytical session, a calibration curve was freshly generated.

The analytical method showed a Limit of Quantitation (LOQ) of 0.10 IU/mL and a linearity concentration range of 0.10 IU/mL-0.50 IU/mL. Sample solutions were analyzed undiluted or diluted with water to fulfil calibration curve range. The results are reported in Table 1

Table 1 summarizes the results of the experiment in which a solution of heparin was placed in the donor chamber of the Franz Cell System.

TABLE 1

| Sample | Conc. (IU/mL) | Amount permeated (IU/cm$^2$) |
|---|---|---|
| Sample 1 (Blank) | <LOQ | ND |
| Sample 2 | <LOQ | ND |
| Sample 3 | <LOQ | ND |
| Sample 4 | 0.108 | 0.43 |
| Sample 5 | 0.141 | 0.56 |
| Sample 6 | 0.177 | 070 |

ND = non-detectable

In 3 out of 5 test cells, heparin was detectable in the receiving chamber at concentrations close to LOQ (0.1 IU/mL). The results indicate that this model is suitable to measure possible heparin permeability. Under the experimental conditions employed, heparin in solution shows negligible permeability, if any.

Table 2 below reports the results of the experiment in which samples of Flector-Heparin Patch were tested for heparin permeability in the Franz Cell System. In this experiment, heparin was not detectable in the receiving chamber. The combination of the two findings, i.e., permeability of heparin from a solution (although negligible) but not from the patch, leads to the conclusion that heparin is not released from the patch.

TABLE 2

| Sample | Conc. (IU/mL) | Amount permeated (IU/cm$^2$) |
|---|---|---|
| Sample 1 (Blank: Flector ®) | <LOQ | ND |
| Sample 2 (Flector-Heparin) | <LOQ | ND |
| Sample 3 (Flector-Heparin) | <LOQ | ND |
| Sample 4 (Flector-Heparin) | <LOQ | ND |
| Sample 5 (Flector-Heparin) | <LOQ | ND |
| Sample 6 (Flector-Heparin) | <LOQ | ND |

ND = non-detectable

Tables 3 and 4 report the linear regression slopes that describe the DHEP permeation rate (µg/cm 2/h), obtained from RUN 1 and RUN 2, resulting from the comparison test between Flector-Heparin Patch (Test, T) and Flector® Patch (Reference, R).

TABLE 3

Regression Slopes from RUN 1

| SAMPLE | SLOPE (µg/cm$^2$/h) |
|---|---|
| 1T | 18.6616 |
| 2R | 6.2625 |
| 3T | 17.7630 |
| 4R | 5.7784 |
| 5T | 17.3546 |
| 6R | 6.4551 |

TABLE 4

Regression Slopes from RUN 2

| SAMPLE | SLOPE (µg/cm$^2$/h) |
|---|---|
| 1R | 6.1740 |
| 2T | 15.4304 |
| 3R | 5.3828 |
| 4T | 13.1571 |
| 5R | 6.7123 |
| 6T | 14.0885 |

In this study, the permeation of diclofenac epolamine (DHEP) was assessed in vitro with Flector® and Flector-Heparin patches by using a Franz Cell System, according to the FDA Guidance for Industry on Non sterile Semisolid Dosage Forms[1]. According to the non-parametric method of the FDA Guidance, Fleeter-Heparin Patch was not found to be equivalent to Flector® Patch in terms of DHEP release and permeability. The mean DHEP permeation flow rate over 24 hours was higher from the Flector-Heparin Patch than the Flector® Patch (2.01±0.60 vs. 0.86±0.19 µg/cm2/h). Also, the cumulative amount of DHEP that crossed the Franz Cell silicone membrane over 24 hours was significantly greater for Flector-Heparin Patch than Flector® Patch (48.23±14.37 vs. 20.54±4.68 µg/cm2). Heparin did not appear to be released from the plaster.

In conclusion, the results of the in vitro permeation tests demonstrate that heparin contained in the FlectorHeparin Patch enhances DHEP release and subsequent membrane permeation. This observation is consistent with findings from several phase 3 clinical trials of greater pain relief in minor soft tissue injury patients following Flector-Heparin Patch application to the site of injury, as opposed to treatment with the Flector® Patch.

Example 2

The experiment described in Example 1 was repeated using a Franz Cell System fitted with a thinner silicone membrane (0.25 mm instead of 0.5 mm) to allow greater passage of heparin from a control solution, with heparin content being determined as described in Example 1.

Table 5 below summarizes the results of the experiment in which a heparin solution was placed in the donor chamber of the Franz Cell System.

TABLE 5

| Sample | Conc. (IU/ml) | Amount permeated (IU/cm$^2$) |
| --- | --- | --- |
| Sample 2 (cell 2) | 0.1107 | 1.11 |
| Sample 3 (cell 3) | 0.1247 | 1.25 |
| Sample 4 (cell 4) | 0.1517 | 1.52 |
| Sample 4 (cell 4) | 0.1119 | 1.12 |
| Sample 5 (cell 5) | 0.1361 | 1.36 |

ND = non-detectable

| Blank (buffer pH 7.4) | Conc. IU/ml | % Heparin Permeated |
| --- | --- | --- |
| Sample 1 (cell 1) | <LOQ | ND |

In all 5 tests cells (2 through 6), heparin was detected in the receiving chamber at concentrations slightly above the LOQ (0.1 IU/ml).

In Table 6 below are reported the results of the experiment in which samples from Flector-Heparin Patch were tested to investigate heparin permeability in the Franz Cell System. In this experiment, heparin was not detected in the receiving chamber (<LOQ).

TABLE 6

| Sample | Conc. Permeated (IU/ml) | Amount of Heparin permeated (IU/cm$^2$) |
| --- | --- | --- |
| Sample 1 (Blank: Fector ®) cell 1 | <LOQ | ND |
| Sample 2 (Flector-Heparin) cell 2 | <LOQ | ND |
| Sample 3 (Flector-Heparin) cell 3 | <LOQ | ND |
| Sample 4 (Flector-Heparin) cell 4 | <LOQ | ND |
| Sample 5 (Flector-Heparin) cell 5 | <LOQ | ND |
| Sample 6 (Flector-Heparin) cell 6 | <LOQ | ND |

ND = non-detectable

The results of this permeation study confirm the findings described in Example 1, in that all 5 patch receiving cells had a heparin concentration below the limit of quantitation, while all those from the aqueous solution were above 1%, supporting the conclusion that, in the worst case, no more than 0.7 IUs of heparin could have left the patch. Furthermore, when residual heparin content was measured in Flector-Heparin Patch specimens following 24 hours of application to the silicone membrane in five cells, the results indicated that the entire amount was retained (results not shown).

Example 3

Assessment of Residual DHEP and Heparin Content in Flector-Heparin Patches after Application to Healthy Subjects a) DHEP Analysis One Flector-Heparin patch was cut into pieces of 1 cm2 and extracted with methanol under reflux for one hour at 75° C. This procedure was repeated 3 times. The HPLC/UV analysis was performed with a Symmetry shield RP 18, 5 µm, 150×3.9 mm chromatography column and pH 3.5 acetate buffer/acetonitrile (525/475 v/v) as mobile phase. The flow rate was 1.0 ml/min and the UV detector wavelength at A 275 nm. The injection volume was 20 µL and the retention time of diclofenac peak of 9.0 minutes±10% with area accuracy of: S 2% as from validation data.

The validation range of this method falls within the 80-120(%) of the declared DHEP content of patches. On the basis of the in vitro permeation study of DHEP, performed with a synthetic membrane, the expected amount of DHEP absorbed in the skin application study would not be higher than 20% of the declared content of the patch. Therefore, linearity, accuracy and precision of the DHEP assay analytical method were respected and this method was applied without generating a multi-point calibration curve.

b) Heparin Analysis

One Flector-Heparin patch was cut into pieces of 1 cm2 and extracted with 500 mL of Acetate buffer pH 7 under stirrer for 16 hours. The sample preparation was performed by transferring 1 mL of suspension in a plastic vial and then it was centrifuged at 13000 rpm for 10 minutes. Heparin content was determined with HPLC-UV after enzymatic reaction with Heparinase I at 37° C. for 3 hours.

Heparinase is selective for the cleavage of the glycosidic bond between hexosamines and uronic acids generating a double bond on the non-reducing end of the uronic acid that absorbs at 232 nm permitting the detection of oligosaccharides and disaccharides chains. After the reaction, the analysis was performed using a HPLC/UV system equipped with a Siligel SAX 5 µm, 150×4.6 mm chromatography column with pre-column Uptistrategy C18-2, 5 µm, 10×4 mm/AGK 10/04-2. The mobile phase was sodium chloride 60 mM at pH 4.0 with sodium chloride 1.2 M at pH 4.0 combined in a gradient. The flow was 1 mL/min with UV detector wavelength at A. 232 nm and the injection volume 20 µL with area accuracy of: S 10% as from validation data.

A validated analytical method for the heparin assay into Flector-Heparin patches was applied in this study for the heparin residual dose measurements.

c) Results

Results are referred to patches applied to volunteers arms for 24 hours (Test) compared to patches of the same envelope not applied (references).

In details, one envelope, containing 5 patches, was provided for each subject. Two of 5 patches were applied by the investigator to the inner part of the upper arms of the subject. One applied patch was analyzed to evaluate DHEP residual content, the other was analyzed for Heparin residual content. One patch was analyzed at time zero of DHEP content and one patch of the three remaining patches was analyzed as time zero of Heparin content.

Table 7 shows the DHEP content value for 24 Flector-Heparin patches analyzed before topical treatment and after 24 hours topical application in 24 volunteers.

TABLE 7

| | Time0 | | After 24 hours topical application | | |
|---|---|---|---|---|---|
| Subject No. | DHEP mg | Assay % | Subject | DHEP mg | Assay % |
| 1 | 172.28 | 95.18 | 1left arm | 169.54 | 93.67 |
| 2 | 168.95 | 93.34 | 2left arm | 169.61 | 93.71 |
| 3 | 173.20 | 95.69 | 3left arm | 169.72 | 93.77 |
| 4 | 176.13 | 97.31 | 4left arm | 163.99 | 90.6 |
| 5 | 170.31 | 94.09 | 5left arm | 164.71 | 91.00 |
| 6 | 168.79 | 93.25 | 6left arm | 169.48 | 93.64 |
| 7 | 177.23 | 97.92 | 7left arm | 167.79 | 92.70 |
| 8 | 174.63 | 96.48 | 8left arm | 167.46 | 92.52 |
| 9 | 182.48 | 100.82 | 9left arm | 169.22 | 93.49 |
| 10 | 185.88 | 102.70 | 10left arm | 167.60 | 92.60 |
| 11 | 173.04 | 95.60 | 11left arm | 166.23 | 91.84 |
| 12 | 171.83 | 94.93 | 12left arm | 167.40 | 92.49 |
| 13 | 181.78 | 100.43 | 13right arm | 165.46 | 91.41 |
| 14 | 174.84 | 96.60 | 14right arm | 165.27 | 91.31 |
| 15 | 170.17 | 94.02 | 15right arm | 166.00 | 91.71 |
| 16 | 174.82 | 96.59 | 16right arm | 169.68 | 93.75 |
| 17 | 177.97 | 98.33 | 17right arm | 171.52 | 94.76 |
| 18 | 176.50 | 97.51 | 18right arm | 168.74 | 93.23 |
| 19 | 178.64 | 98.70 | 19right arm | 170.01 | 93.93 |
| 20 | 187.61 | 103.65 | 20right arm | 169.38 | 93.58 |
| 21 | 170.65 | 94.28 | 21right arm | 175.35 | 96.88 |
| 22 | 171.34 | 94.66 | 22right arm | 171.10 | 94.53 |
| 23 | 177.58 | 98.11 | 23right arm | 170.76 | 94.34 |
| 24 | 166.88 | 92.20 | 24right arm | 171.94 | 94.99 |
| Mean | 175.15 | 96.77 | Mean | 168.66 | 93.19 |
| RSD | 5.35 | | RSD | 2.60 | |
| CV % | 3.06 | | CV % | 1.60 | |

The DHTEP loss, after 24 hour of topical application, measure as % of the declared assay was about 3.6%.

Table 8 hereinbelow shows the heparin content value for 24 Flector-Heparin, analyzed before topical treatment and after 24 hours topical application in 24 volunteers.

TABLE 8

| | Time0 | | After 24 hours topical application | | |
|---|---|---|---|---|---|
| Subject No. | Heparin IU | Assay % | Subject | Heparin IU | Assay % |
| 1 | 5226 | 93.32 | 1right arm | 5210 | 93.04 |
| 2 | 5010 | 89.46 | 2right arm | 5311 | 94.84 |
| 3 | 5203 | 92.91 | 3right arm | 5709 | 101.95 |
| 4 | 5917 | 105.66 | 4right arm | 5782 | 103.25 |
| 5 | 5569 | 99.45 | 5right arm | 6163 | 110.05 |
| 6 | 5246 | 93.68 | 6right arm | 5822 | 103.96 |
| 7 | 5839 | 104.27 | 7right arm | 61.02 | 108.96 |
| 8 | 5193 | 5193 | 8right arm | 5408 | 96.57 |
| 9 | 5672 | 101.29 | 9right arm | 5674 | 101.32 |
| 10 | 5421 | 96.80 | 10right arm | 5826 | 104.04 |
| 11 | 6105 | 109.02 | 11right arm | 5522 | 98.61 |
| 12 | 5625 | 100.45 | 12right arm | 5526 | 98.68 |
| 13 | 5297 | 94.59 | 13left arm | 5356 | 95.64 |
| 14 | 5163 | 92.20 | 14left arm | 4819 | 86.05 |
| 15 | 5934 | 105.96 | 15left arm | 5420 | 96.79 |
| 16 | 5919 | 105.70 | 16left arm | 5449 | 97.30 |
| 17 | 5801 | 103.59 | 17left arm | 5869 | 104.80 |
| 18 | 6052 | 108.07 | 18left arm | 6251 | 111.63 |
| 19 | 5633 | 100.59 | 19left arm | 5517 | 98.52 |
| 20 | 5967 | 106.55 | 20left arm | 6182 | 110.39 |
| 21 | 5372 | 95.93 | 21left arm | 5699 | 101.77 |
| 22 | 5033 | 89.88 | 22left arm | 5305 | 94.73 |
| 23 | 5712 | 102.00 | 23left arm | 5071 | 90.55 |
| 24 | 6125 | 109.38 | 24left arm | 5920 | 105.71 |
| Mean | 5585 | 99.73 | Mean | 5621 | 100.38 |
| RSD | 356.3 | | RSD | 363.5 | |
| CV % | 6.4 | | CV % | 6.5 | |

The heparin assay loss, after 24 hours of topical application, was inconsistent. Form the above results it can be seen that heparin is not released from the plaster after topical application. Thus, after 24 hours a loss of DHEP content was measured into test patches in comparison to the references patches demonstrating that DHEP was absorbed through the skin. After 24 hours topical application of patches the DHEP loss was, in facts, about 3.6%. On the contrary, the results on heparin assay loss, after 24 hours of topical application demonstrated that heparin does not permeate in vitro. The same mechanism occurred in vivo.

Example 4

Effects of a plaster containing diclofenac epolamine (DHEP) and heparin on the pain threshold in asymptomatic subjects (no spontaneous pain) with latent algogenic condition (subcutaneous and/or muscle hyperalgesia and dystrophic changes) of the lower limb.

The study plan included three visits at the clinics, which took place at screening/randomization (Visit T0/T, day 1), after 3 days of medicated plasters application (Visit T4, day 4) and after 7 days of medicated plasters application (Visit T8, day 8, final visit).

Subjects of either sex, aged between 18 and 65 years, having no spontaneous pain since one month before the enrolment, with hyperalgesia and trophic changes of deep somatic structures from latent algogenic conditions of the lower limbs.

A total number of 104 subjects were screened for enrolment in this study and were randomized—equally distributed—to one of the four treatments: 26 subjects (25% of total population) therefore constituted each group.

EFFICACY RESULTS: The four treatment groups were well matched for demographic and other baseline characteristics, with gender distribution and thickness of subcutis being the only exceptions and were therefore included as covariates in the statistical models. Noteworthy, the mean value of the baseline pain threshold to electrical stimulation of the muscle confirm the presence of a latent algogenic condition in the enrolled subjects, if compared to normal values.

The results of the primary variable 'pain threshold to electrical stimulation of the muscle confirm the ability of the DHEP plaster to increase the pain threshold of volunteers with latent algogenic condition as compared to placebo (p=0.0299), in agreement with previous data, and showed a significantly more marked increase in the DHEP Heparin group as compared to the other groups over the treatment period both in the ITT (Table 9) and PP population.

The difference in efficacy was statistically significant in favor of the DHEP Heparin group as compared to DHEP (p=0.0307), Heparin (p=0.002) and placebo (p<0.0001) over the 7-day treatment period. Moreover, the difference between Heparin and placebo was not significant (p=0.2568). Finally, for the pain threshold to electrical stimulation in cutis and subcutis, the increase of pain thresholds was generally more marked for the DHEP-containing medicated plasters as compared to those not containing DHEP, although the analyses did not reveal any statistically significant difference between groups.

Table 9: Adjusted mean values for change from baseline of pain threshold to electrical stimulation of muscle as compared to the mean values without adjustment for the covariates.

TABLE 9

| Muscle (mA) | DHEP Heparin | DHEP | Heparin | Placebo |
|---|---|---|---|---|
| Day 4 (Mean ± SD) | 0.29 ± 0.38 | 0.15 ± 0.27 | 0.06 ± 0.33 | −0.09 ± 0.43 |
| Day 4 (Adjusted Mean for Gender) | 0.27 | 0.13 | 0.03 | −0.12 |
| Day 4 (Adjusted Mean for Subcutis thickness) | 0.28 | 0.15 | 0.06 | −0.09 |
| Day 8 (Mean ± SD) | 0.40 ± 0.46 | 0.16 ± 0.38 | 0.06 ± 0.38 | −0.02 ± 0.28 |
| Day 8 (Adjusted Mean for Gender) | 0.38 | 0.14 | 0.03 | −0.04 |
| Day 8 (Adjusted Mean for Subcutis thickness) | 0.40 | 0.17 | 0.06 | 0.00 |

The comparison between groups on mean changes from baseline after 3 and 7 days of treatment for both primary and secondary efficacy parameters was performed by means of an ANCOVA model with baseline values as a covariate.

The compliance to study treatment was calculated and the comparisons between groups were performed after 7 days of treatment by means of the $Chi^2$ test.

Adverse events were coded using MedDRA dictionary. The System Organ Class (SOC) and Preferred Term (PT) were used for tabulation. The difference between treatment groups in the proportion of patients who experienced adverse events and serious adverse events was evaluated using $Chi^2$ test.

A descriptive analysis of vital signs (blood pressures and hearth rate) by-visit was performed. The results of the secondary variables 'pain threshold to mechanical (pressure) stimulation in muscle' and 'thickness of muscle at ultrasound examination' did not show any statistically significant differences between treatment groups during the study period.

Although the 'thickness of subcutis measurements at post-treatment ultrasound examination' showed statistically significant differences between heparin group and the other groups, the clinical relevance of such a finding is not clear considering the presence of statistically significant pre-treatment intergroup differences.

The results support a superior effect of the new DHEP Heparin plaster in comparison to the DHEP plaster in increasing the pain threshold to electrical stimulation at muscle level on volunteers with latent algogenic condition of the quadriceps muscle following a once-a-day plaster application for 7 consecutive days. A 30% increase in pain threshold as compared to the pre-treatment value was reported in the DHEP Heparin treated subjects, while the increase was only 12% in subjects treated with DHEP plaster. Differently from a plaster containing heparin only, both DHEP medicated plasters were found to be significantly more effective than placebo.

We claim:

1. A method of administering diclofenac from a transdermal patch containing diclofenac and heparin, the method comprising:
 a) assessing a test transdermal patch containing diclofenac and heparin using an in vivo method of quantifying the relative release of diclofenac and heparin to demonstrate that the test transdermal patch has release characteristics comprising:
  (i) retention of all of the heparin after releasing diclofenac, and
  (ii) release of a higher amount of diclofenac compared to a transdermal patch comprising diclofenac but not heparin; and
 b) topically applying a treatment transdermal patch containing diclofenac and heparin that is equivalent to the test transdermal patch to the skin of a subject for no more than 24 hours,
 wherein the test transdermal patch and the treatment transdermal patch each comprise:
  a substrate layer;
  an adhesive layer in the form of a polymeric hydrogel matrix, the adhesive layer comprising:
   an effective amount of diclofenac or a pharmaceutically acceptable salt thereof,
   sodium ethylenediamine tetraacetate,
   heparin,
   at least one thickening agent,
   at least one wetting agent, and
   at least one cross-linking agent; and
  a protective film which can be removed at the moment of use; and
 wherein the in vivo method of quantifying the relative release of diclofenac and heparin from the test transdermal patch comprises the steps:
  topically applying the test transdermal patch to the skin of a test subject for no more than 24 hours;
  measuring residual content of diclofenac in the test transdermal patch after topical application to determine the amount of diclofenac released from the test transdermal patch;
  measuring residual content of heparin in the test transdermal patch after topical application to determine all of the heparin is retained in the test transdermal patch after 24 hours of topical application; and
  comparing the amount of diclofenac released with the amount of heparin retained in the test transdermal patch.

2. The method of claim 1, wherein the diclofenac or pharmaceutically acceptable salt thereof is diclofenac epolamine.

3. The method of claim 1, wherein the effective amount of the diclofenac epolamine is between 0.1 and 5 wt % with respect to the hydrogel matrix.

4. The method of claim 3, wherein the effective amount of the diclofenac epolamine is between 0.3 and 3 wt % with respect to the hydrogel matrix.

5. The method of claim 1, wherein the concentration of the heparin is between 0.05 and 1 wt % with respect to the hydrogel matrix.

6. The method of claim 1, wherein the subject has a minor soft tissue injury.

7. The method of claim 1, wherein the subject has a minor strain, sprain, or contusion.

8. The method of claim 1, wherein the amount of diclofenac or pharmaceutically acceptable salt thereof released from the test transdermal patch after 24 hours of topical application was determined to be about 3.6%.

* * * * *